United States Patent [19]

Ura et al.

[11] 4,376,202
[45] Mar. 8, 1983

[54] ANILINE DERIVATIVE AND PROCESS FOR PRODUCTION THEREOF

[75] Inventors: Yasukazu Ura; Gojyo Sakata; Kenji Makino; Yasuo Kawamura; Kazuya Kusano; Jun Satow, all of Funabashi, Japan

[73] Assignee: Nissan Chemical Industries, Ltd., Tokyo, Japan

[21] Appl. No.: 275,849

[22] Filed: Jun. 22, 1981

[30] Foreign Application Priority Data

Oct. 24, 1980 [JP]   Japan .................................. 55-149014

[51] Int. Cl.$^3$ .................. C07D 241/44; C07D 215/22; A01N 43/60; A01N 43/42
[52] U.S. Cl. ..................................... 544/354; 546/157; 424/250; 424/258
[58] Field of Search ......................................... 544/354

[56] References Cited

U.S. PATENT DOCUMENTS 3,900,473  8/1975  Piel et al. ........................... 544/353

FOREIGN PATENT DOCUMENTS 52-72821  6/1977  Japan .
55-98153  7/1980  Japan .

OTHER PUBLICATIONS

Anderson et al., J.C.S. Perkins I, 1974, 129.

*Primary Examiner*—Mark L. Berch
*Attorney, Agent, or Firm*—Stevens, Davis, Miller & Mosher

[57] ABSTRACT

An aniline derivative represented by the formula (I):

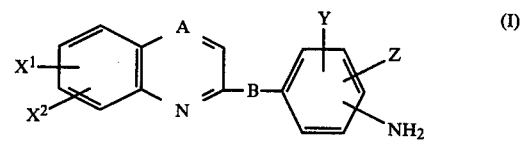

wherein A denotes CH or nitrogen atom; B denotes oxygen atom or sulfur atom; $X^1$ and $X^2$, independently of each other, denote hydrogen atom, halogen atom, trifluoromethyl group or nitro group; Y and Z, independently of each other, denote hydrogen atom or halogen atom, and a process for producing the same.

7 Claims, No Drawings

4,376,202

ANILINE DERIVATIVE AND PROCESS FOR PRODUCTION THEREOF

BACKGROUND OF THE INVENTION (1) Field of the Invention

This invention relates to aniline derivatives having a quinoline or quinoxaline skeleton and a process for production thereof.

(2) Description of the Prior Art

Such compounds as described, for example, in Japanese Patent Application Laid-Open No. 72821/1977 have been known as phenoxyquinoline derivatives. These compounds, however, have none of an amino group as their substituent group.

The present inventors have found new aniline derivatives which are intermediates of new compounds useful for insecticides and a process for producing said derivative.

The present invention relates to intermediates which are the starting material of the compounds described in co-pending U.S. patent application "Heterocyclic ether or thioether linkage containing urea compounds, process for producing same and insecticides containing said compounds" filed on May 26, 1981 under Ser. No. 267,077.

SUMMARY OF THE INVENTION

An object of this invention is to provide a new quinoline or quinoxaline skeleton having aniline derivatives, which are intermediates of compounds effective as insecticides.

More specifically, the object of the present invention is to provide aniline derivatives of the following formula (I):

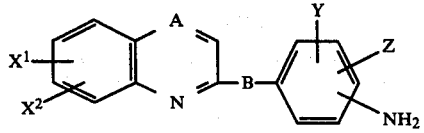

wherein A denotes CH or nitrogen atom; B denotes oxygen atom or sulfur atom; $X^1$ and $X^2$, independently of each other, denote hydrogen atom, halogen atom, trifluoromethyl group or nitro group; and Y and Z, independently of each other, denote hydrogen atom or halogen atom.

Another object of the invention is to provide a process for producing new quinoline or quinoxaline skeleton having aniline derivatives expressed by the above formula (I).

These and other objects of the present invention will be more apparent from the following detailed description and examples.

DETAILED DESCRIPTION OF THE INVENTION

The present invention relates to aniline derivatives of the following formula (I):

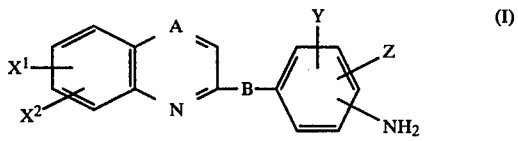

wherein A denotes CH or nitrogen atom; B denotes oxygen atom or sulfur atom; $X^1$ and $X^2$, independently of each other, denote hydrogen atom, halogen atom, trifluoromethyl group or nitro group; and Y and Z, independently of each other, denote hydrogen atom or halogen atom.

The new compounds of the above formula (I) are intermediates of the compounds of the following formula (IV) which are described in the aforesaid co-pending U.S. patent application "Heterocyclic ether or thioether linkage containing urea compounds, process for producing same and insecticides containing said compounds", and is an intermediate product of a new compound, which is useful in insecticides.

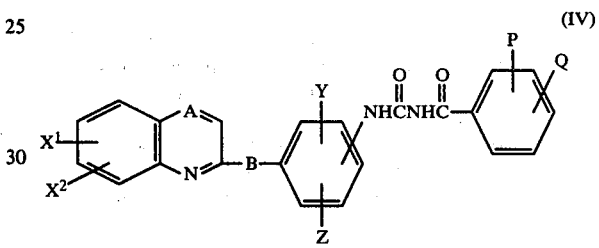

wherein A, B, $X^1$, $X^2$, Y and Z have the same meanings as above; P and Q, independently of each other, denote hydrogen atom, halogen atom, alkoxy group or alkyl group.

The new compounds of the above-mentioned formula IV are exceedingly useful as agents for controlling and combating sanitary insect pests as well as insect pests of forest, insect pests in stored crops and agricultural and horticultural insect pests which damage paddy-rice plants, vegetables, fruit trees, cotton plants and other crops and flowering plants.

In the compound of this invention, it is significant that the benzene ring, which is bonded with the quinoline or quinoxaline skeleton via the oxygen or sulfur atom, has an amino group. This amino group contributes to the reaction to permit the present compounds to become intermediates of new compounds of the aforesaid formula IV which are useful as insecticides. No compound as represented by the formula IV is obtainable from the compounds having no amino group.

The quinoline or quinoxaline skeleton having aniline derivatives of the invention can be produced in a manner shown by the following reaction formula:

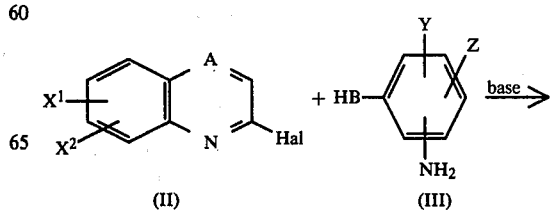

-continued

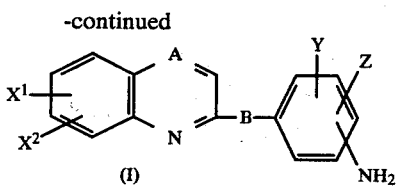

(I)

wherein $X^1$, $X^2$, Y, Z, A and B have the same meanings as above, and "Hal" denotes a halogen atom.

That is, the compound of the formula I can be produced by adding a base to an aniline derivative of the formula III in the presence of an organic solvent such as dimethylformamide or dimethylsulfoxide which is inert to the reactants, to obtain, for instance, the potassium salt or sodium salt thereof; and then adding a compound of the formula II to allow a condensation reaction with the salt thus obtained.

The reaction temperature is preferably from room temperature to 100° C. and particularly preferably from 40° C. to 70° C.

The quantity of the base used in the reaction may be used 1–1.1 times by mol that of the compound of the formula III.

The product may be isolated after the reaction, for instance, by introducing the reaction solution into water and filtering off the precipitated solid, and if need be, may be purified in a suitable manner.

From the compound of the general formula I, the compound of the aforesaid formula IV can be synthesized by condensation-reacting a benzoyl isocyanate of the following formula (V):

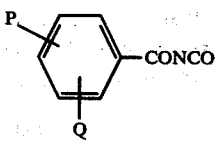

(V)

wherein P and Q have the aforesaid meanings, with a quinoline or quinoxaline skeleton having an aniline derivative of the formula I, preferably, in the presence of a solvent inert to the reactants.

The present invention will be further explained below with reference to examples, but is not limited to these examples.

EXAMPLE 1

Synthesis of 4-(6-fluoro-2-quinolyloxy)-aniline of the following formula:

(Compound No. 4)

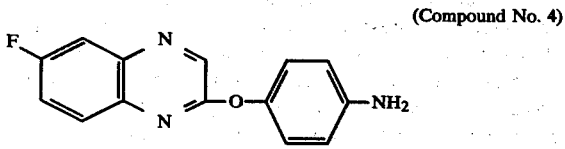

6.6 g (0.06 mol) of p-aminophenol in 4.0 g (0.06 mol) potassium hydroxide (purity 85%) and 80 ml of dimethylsulfoxide was heated under stirring. The water generated was distilled off under reduced pressure to obtain the potassium p-aminophenolate. To the solution, which was allowed to be cooled to room temperature, was added a solution of 10.9 g (0.06 mol) of 6-fluoro-2-chloroquinoxaline dissolved in 60 ml of dioxane. The mixture was reacted at 50°–60° C. for 3 hours. After the reaction was over, the reaction solution was poured onto ice and the separated solid was filtered off, and washed with 5% aqueous solution of sodium hydroxide and then washed with water. The substance thus obtained was recrystallized from ethanol to yield 8.2 g (yield 54%) of the intended compound (Compound No. 4) having a melting point of 174°–175.5° C. as light-yellow crystals.

EXAMPLE 2

Synthesis of 3,5-dichloro-4-(6-chloro-2-quinoxalyloxy)-aniline of the following formula:

(Compound No. 9)

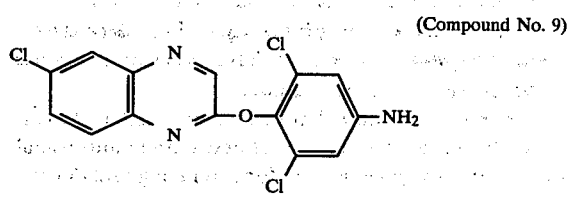

9.0 g (0.05 mol) of 3,5-dichloro-4-hydroxyaniline in 3.3 g (0.05 mol) of 85% potassium hydroxide and 80 ml of dimethylsulfoxide was heated under stirring. The water generated was distilled off under reduced pressure to obtain the potassium salt of 3.5-dichloro-4-hydroxyaniline. Then, to the solution which was allowed to be cooled to room temperature was added a solution of 9.9 g (0.05 mol) of 2,6-dichloroquinoxaline dissolved in 60 ml of dioxane. The mixture was subjected to reaction at 55°–65° C. for 4 hours. After the reaction was over, the reaction solution was poured onto ice and 50 ml of 5% solution of sodium hydroxide was added thereto. The solid formed was filtered off and washed with water. This substance was dissolved in heated ethanol. After removing the insoluble matter, the ethanol was distilled away. The resulting crystal was recrystallized from benzene to produce 7.3 g (yield 43%) of the intended compound (Compound No. 9) as white crystals, m.p. 187°–189° C.

EXAMPLE 3

Synthesis of 3-chloro-4-(2-quinolyloxy)-aniline of the following formula:

(Compound No. 14)

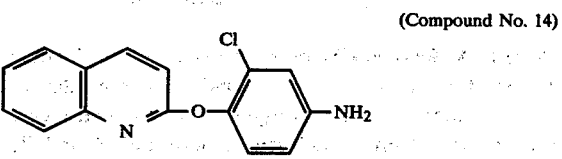

8.6 g (0.06 mol) of 3-chloro-4-hydroxyaniline in 4.0 g (0.06 mol) of 85% potassium hydroxide and 80 ml of dimethylsulfoxide was heated under stirring. The water generated was distilled away under reduced pressure to obtain the potassium salt of 3-chloro-4-hydroxyaniline. Then, to the solution which was allowed to be cooled to room temperature was added a solution of 9.8 g (0.06 mol) of 2-chloroquinoline dissolved in 60 ml of dimethylsulfoxide. The mixture was reacted at 75°–85° C. for 8 hours. After the reaction was over, the reaction solution was poured onto ice. After 60 ml of 5% aqueous solution of sodium hydroxide was added to the reaction solution, the formed solid was filtered off and washed with water. The substance was recrystallized from ethanol to produce 7.8 g (yield 48%) of the intended compound (Compound No. 14) as white crystals, m.p. 144°–145° C.

EXAMPLE 4

Synthesis of 4-(6-chloro-2-quinoxalylthio)-aniline of the following formula:

(Compound No. 10)

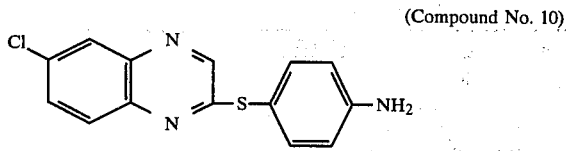

5.7 g (0.045 mol) of p-aminothiophenol together with 3 g (0.045 mol) of 86% potassium hydroxide and 2 ml of water in 80 ml of dimethylsulfoxide was heated under stirring at 80°–90° C. for 5 hours to make the potassium p-aminothiophenolate. The water generated was removed off by azeotropic distillation under reduced pressure. To this solution which was allowed to be cooled to room temperature was added a solution of 9 g (0.045 mol) of 2,6-dichloroquinoxaline dissolved in 100 ml of dimethylsulfoxide. The mixture was subjected to the reaction, while stirring, at 80°–90° C. for 8 hours. After the reaction mixture was cooled to the room temperature, it was poured into a great deal of water and stirred. The precipitating solid was filtered off, washed with 5% aqueous solution of sodium hydroxide and then washed with water, followed by drying. The crude crystals thus obtained were recrystallized from a mixed solution of ethanol-benzene to produce 6.7 g (yield 52%) of the intended compound (Compound No. 10) as light-yellow crystals, m.p. 144°–147° C.

EXAMPLE 5

Synthesis of 3-(6-chloro-2-quinoxalyloxy)-aniline of the following formula:

(Compound No. 18a)

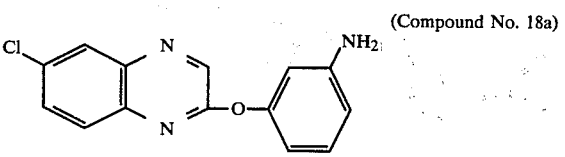

6.6 g (0.06 mol) of m-aminophenol in 4.0 g (0.06 mol) of 85% potassium hydroxide and 80 ml of dimethylsulfoxide was heated under stirring. The water generated was distilled away under reduced pressure to make the potassium m-aminophenolate. To the solution which was allowed to cool to room temperature was added a solution of 11.9 g (0.06 mol) of 2,6-dichloroquinoxaline dissolved in 80 ml of dioxane. The mixture was reacted at 50°–60° C. for 5 hours. After the reaction was over, the reaction mixture was poured into ice and cold water. The formed solid was filtered off and washed with 5% aqueous solution of sodium hydroxide and then washed with water. The crude crystals thus obtained were recrystallized from ethanol, to produce 8.8 g (yield 54%) of white crystals, m.p. 119°–120° C.

In a similar manner to that of the above examples, the compounds shown in the following tables were synthesized.

TABLE 1

Syntheses of the compounds of the following formula:

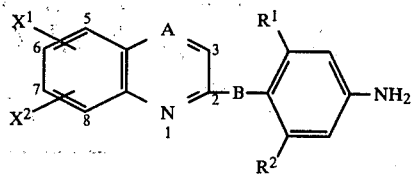

| Compound No. | A | B | X¹ | X² | R¹ | R² | Appearance | Melting point (°C.) |
|---|---|---|---|---|---|---|---|---|
| 1 | N | O | H | H | H | H | light-yellow crystal | 156.5–158 |
| 2 | N | S | H | H | H | H | light-yellow crystal | 169–171 |
| 3 | N | O | H | H | Cl | Cl | white crystal | 182–185 |
| 5 | N | O | 6-F | H | Cl | H | white crystal | 179–180 |
| 6 | N | O | 6-F | H | Cl | Cl | white crystal | 192–194.5 |
| 7 | N | O | 6-Cl | H | H | H | light-yellow crystal | 148–150 |
| 8 | N | O | 6-Cl | H | Cl | H | white crystal | 163–164 |
| 11 | N | O | 6-CF₃ | H | Cl | H | white crystal | — |
| 12 | N | O | 6-NO₂ | H | Cl | Cl | white crystal | 209–211 |
| 13 | CH | O | H | H | H | H | white crystal | 163–164 |
| 15 | CH | O | H | 7-CF₃ | Cl | H | white crystal | 231–235 |
| 16 | CH | O | 3-Cl | 6-Cl | H | H | white crystal | 192–195 |
| 17 | N | S | 6-Cl | H | H | H | white crystal | 144–147 |

TABLE 2

Syntheses of the compounds of the following formula:

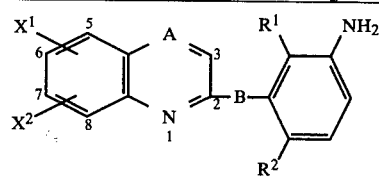

| Compound No. | A | B | X¹ | X² | R¹ | R² | Appearance | Melting point (°C.) |
|---|---|---|---|---|---|---|---|---|
| 18 | N | O | 6-Cl | H | H | Cl | white crystal | 140–142 |
| 19 | N | O | 6-CF₃ | H | H | H | white crystal | 105–106 |
| 20 | CH | O | 6-Br | H | H | H | white crystal | 114–116 |
| 21 | N | S | 6-F | H | H | H | white crystal | 121–123 |
| 22 | CH | O | H | H | H | H | white crystal | 123–124 |
| 23 | N | O | 6-F | H | H | H | white crystal | 149–150 |
| 24 | N | O | 6-CF₃ | H | H | Cl | white crystal | 124–126 |
| 25 | CH | O | 6-Cl | H | H | H | white crystal | 110–111 |

REFERENCE EXAMPLE 1

Synthesis of N-(2,6-dichlorobenzoyl)-N'-[4-(2-quinolyloxy)phenyl]urea (Compound No. 42) represented by the following formula:

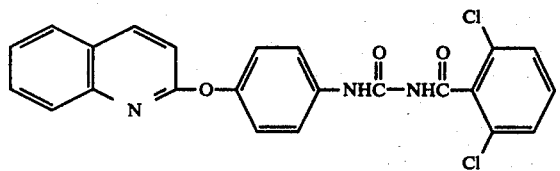

ature, and the crystals obtained were filtered off, washed with acetonitrile and then dried to obtain 1.5 g of white crystals (Compound No. 42), m.p. 234°–235.5° C.

In a similar manner to that of the above Reference example, the compounds shown in the following Table 3 were synthesized.

TABLE 3

Compounds of the following formula (IVa):

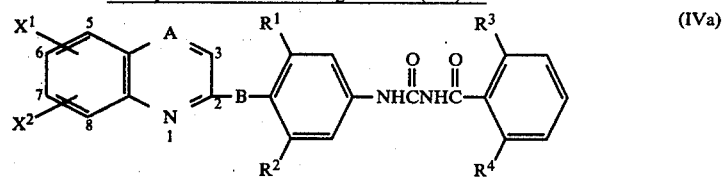

| Compound No. | A | B | $X^1$ | $X^2$ | $R^1$ | $R^2$ | $R^3$ | $R^4$ | Appearance | Melting point (°C.) |
|---|---|---|---|---|---|---|---|---|---|---|
| 26 | N | S | H | H | H | H | Cl | Cl | white crystal | 222–224 |
| 27 | N | S | H | H | H | H | F | F | white crystal | 224–226 |
| 28 | N | O | 6-Cl | H | H | H | F | F | white crystal | 227–228 |
| 29 | N | O | 6-Cl | H | H | H | Cl | Cl | white crystal | 225–226 |
| 30 | N | O | 6-Cl | H | Cl | H | Cl | Cl | white crystal | 239–240 |
| 31 | N | O | 6-Cl | H | Cl | Cl | F | F | white crystal | 229–230 |
| 32 | N | O | 6-Cl | H | Cl | Cl | Cl | H | white crystal | 244–246 |
| 33 | N | O | 6-Cl | H | Cl | Cl | Cl | Cl | white crystal | 255–256 |
| 34 | N | S | 6-Cl | H | H | H | F | F | white crystal | 236–239 |
| 35 | N | O | 6-F | H | H | H | Cl | H | white crystal | 238–239 |
| 36 | N | O | 6-F | H | Cl | H | F | F | white crystal | 227–230 |
| 37 | N | O | 6-F | H | Cl | H | Cl | Cl | white crystal | 245–246 |
| 38 | N | O | 6-F | H | Cl | Cl | F | F | white crystal | 222–225 |
| 39 | N | O | 6-F | H | Cl | Cl | Cl | H | white crystal | 224–225 |
| 40 | N | O | 6-F | H | Cl | Cl | Cl | Cl | white crystal | 241–244 |
| 41 | N | O | 6-CF$_3$ | H | Cl | H | Cl | H | white crystal | 207–210 |
| 43 | CH | O | H | H | Cl | H | F | F | white crystal | 199–201 |
| 44 | N | O | H | H | Cl | Cl | OCH$_3$ | OCH$_3$ | white crystal | 238–242 |

| 45 | | | | | | | | | white crystal | 190–192 |
| 46 | | | | | | | | | white crystal | 210–212 |
| 47 | | | | | | | | | white crystal | 199–201 |
| 48 | | | | | | | | | white crystal | 202–203 |

To a solution of 1.2 g (5.0×10$^{-3}$ mol) of 4-(2-quinolyloxy)aniline dissolved in 40 ml of acetonitrile, was added dropwise with stirring at 0° C., 1.0 g (4.6×10$^{-3}$ mol) of 2,6-dichlorobenzoyl isocyanate. The reaction mixture was reacted overnight at room temper-

REFERENCE EXAMPLE 2

Killing test to Tobacco cutworm larvae

A leaf of cabbage was immersed in a solution of the insecticidally active compound dispersed in water at a predetermined concentration for about 10 sec. The leaf was then picked up and air-dried. The leaf was placed on a moistened filter paper in a Petri dish of 9 cm in diameter. Tobacco cutworm second instar larvae were released on the leaf. The dish closed with the cover was stored in an air-conditioned room at 25° C. with lightings. On the 7th day from the release of the larvae, their life and death were checked. According to the following formula, the mortality was determined and the results obtained are shown in the following Table 4.

$$\text{Mortality} = \frac{\text{number of larvae killed}}{\text{number of larvae placed}} \; 100$$

TABLE 4

| Compounds submitted to test (Compound No.) | Mortality (%) Concentration of active ingredient compound | |
| --- | --- | --- |
| | 10 ppm | 1 ppm |
| Control compound (dichlorobenzuron) | 95 | 20 |
| 26 | 100 | 100 |
| 28 | 100 | 80 |
| 29 | 100 | 100 |
| 30 | 100 | 100 |
| 33 | 100 | 70 |
| 34 | 100 | 50 |
| 36 | 100 | 100 |
| 37 | 100 | 100 |
| 38 | 100 | 100 |
| 39 | 100 | 100 |
| 41 | 100 | 100 |
| 42 | 100 | 50 |
| 44 | 100 | 100 |
| 45 | 100 | 100 |
| 46 | 100 | 100 |
| 47 | 100 | 100 |
| 48 | 100 | 100 |

REFERENCE EXAMPLE 3

In the same manner as in the above-mentioned Reference Example 2, a wet filter paper was laid on a Petri dish of 9 cm in diameter and a leaf of cabbage treated with the solution was placed on the filter paper. After the leaf was air-dried, diamondback moth second instar larvae were released on the leaf. In the same manner as in Test 1, the mortality was determined on the 7th day from the release of larvae and the results shown in the following Table 5 were obtained.

TABLE 5

| Compounds submitted to test (Compound No.) | Mortality (%) Concentration of active ingredient compound | |
| --- | --- | --- |
| | 1000 ppm | 200 ppm |
| Control compound (dichlorobenzuron) | 100 | 20 |
| 26 | 100 | 100 |
| 27 | 100 | 70 |
| 28 | 100 | 100 |
| 29 | 100 | 100 |
| 30 | 100 | 100 |
| 31 | 100 | 100 |
| 32 | 100 | 90 |
| 33 | 100 | 100 |
| 34 | 100 | 100 |
| 35 | 100 | 80 |
| 37 | 100 | 100 |
| 38 | 100 | 100 |
| 39 | 100 | 100 |
| 40 | 100 | 100 |
| 41 | 100 | 100 |
| 42 | 100 | 100 |
| 43 | 100 | 80 |
| 44 | 100 | 100 |

TABLE 5-continued

| Compounds submitted to test (Compound No.) | Mortality (%) Concentration of active ingredient compound | |
| --- | --- | --- |
| | 1000 ppm | 200 ppm |
| 45 | 100 | 100 |
| 46 | 100 | 100 |
| 47 | 100 | 100 |
| 48 | 100 | 100 |

What is claimed is:

1. An aniline derivative represented by the following formula I:

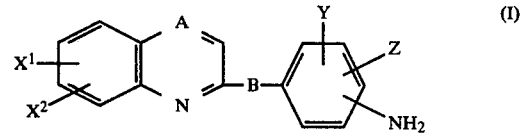

wherein A denotes nitrogen atom; B denotes oxygen atom or sulfur atom; $X^1$ and $X^2$, independently of each other, denote hydrogen atom, halogen atom, trifluoromethyl group or nitro group; and Y and Z, independently of each other, denote hydrogen atom or halogen atom.

2. The aniline derivative of claim 1, wherein B is oxygen atom.

3. The aniline derivative of claim 1, wherein B is sulfur atom.

4. The aniline derivative of claim 1, having the formula:

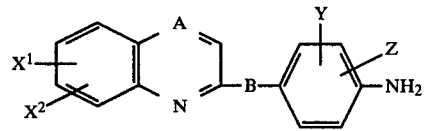

wherein A, B, $X^1$, $X^2$, Y and Z have the same meanings given in claim 1.

5. The aniline derivative of claim 1, having the formula:

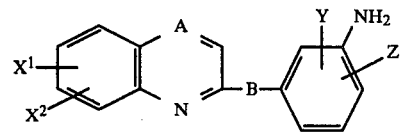

wherein A, B, $X^1$, $X^2$, Y and Z have the same meanings given in claim 1.

6. The aniline derivative of claim 4, having the formula:

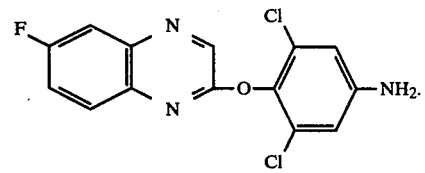

7. The aniline derivative of claim 5, having the formula:

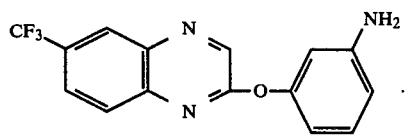

* * * * *